USO05565347A

United States Patent [19]
Fillatti et al.

[11] Patent Number: 5,565,347
[45] Date of Patent: Oct. 15, 1996

[54] TRANSFORMATION AND FOREIGN GENE EXPRESSION WITH PLANT SPECIES

[75] Inventors: JoAnne J. Fillatti; Bruce R. Thomas, both of Davis, Calif.

[73] Assignee: Calgene, Inc., Davis, Calif.

[21] Appl. No.: 113,985

[22] Filed: Aug. 30, 1993

(Under 37 CFR 1.47)

Related U.S. Application Data

[63] Continuation-in-part of Ser. No. 404,723, Sep. 8, 1989, abandoned, which is a continuation-in-part of Ser. No. 872,532, Jun. 10, 1986, abandoned.

[51] Int. Cl.$^6$ .............................. C12N 5/04; C12N 15/84; A01H 4/00
[52] U.S. Cl. ................................ 435/172.3; 435/240.4; 435/240.45; 435/240.51; 435/252.2; 800/205; 800/DIG. 44
[58] Field of Search ........................... 435/172.3, 240.4, 435/240.45, 240.51, 252.2; 800/205, DIG. 44

[56] References Cited

U.S. PATENT DOCUMENTS

| 4,769,061 | 9/1988 | Comai | 71/86 |
|---|---|---|---|
| 4,940,835 | 7/1990 | Shah et al. | 800/205 |

FOREIGN PATENT DOCUMENTS

0120516B1   10/1984   European Pat. Off. .

OTHER PUBLICATIONS

McCormick, et al., "Leaf disc transformation of cultivated tomato (*L. esculentum*) using *Agrobacterium tumefaciens*" *Plant Cell Reports* (1986) 5:81–84.
Gunay and Rao, "In vitro Plant Regeneration from Hypocotyl and Cotyledon Explants of Red Pepper", *Plant Science Letters* (1978) 11:365–372.
Lui et al., "Plant Regeneration from Apple Seedling Explants and Callus Cultures", *Plant Cell Organ Culture* (1983) 2:293–304.
Thomas and Pratt, "Efficient Hybridization Between *Lycopersicon esculentum* and *L. peruvianum* via Embryo Callus",*Theor. Appl. Genet.* (1981) 59:215–219.
Horsch et al., "A Simple and General Method for Transferring Genes into Plants", *Science* (1985) 228: 1229–1231.
Herrera–Estrella et al., "Expression of Chimaeric genes Transferred into Plant Cells using a Ti–Plasmid–derived Vector", *Nature* (1983) 303:209–213.
Fraley et al., "Expression of Bacterial Genes in Plant Cells", *Proc. Natl. Acad. Sci. USA* (1983) 80:4803–4807.
Bevan et al., "A Chimeric Antibiotic Resistance Gene as a Selectable Marker for Plant Cell Transformation", *Nature* (1983) 304:184–187.
Stalker et al., "A Single Amino Acid Substitution in the Enzyme 5–Enolpyruvylshikimate–3–phosphate Synthase Confers Resistance to the Herbicide Glyphosate", *J. Biol. Chem.* (1985) 260:4724–4728.

De Greve et al., "Nucleotide Sequence and Transcript Map of the *Agrobacterium tumefaciens* Ti Plasmid–Encoded Octopine Synthase Gene", *J. Mol. Appl. Genet.* (1983) 1:499–511.
Salomon et al., "Genetic Identification of Functions of TR–DNA Transcripts in Octopine Crown Galls", *EMBO J.* (1984) 3:141–146.
Velten et al., "Isolation of a Dual Plant Promoter Fragment from the Ti Plasmid of *Agrobacterium tumefaciens*" *EMBO J.* (1984) 3:2723–2730.
Garfinkel et al., "Genetic Analysis of Crown Gall:Fine Structure Map of the T–DNA by Site–Directed Mutagenesis", *Cell* (1981) 27:143–153.
Barker et al., "Nucleotide Sequence of the T–DNA Region from the *Agrobacterium tumefaciens* Octopine Ti Plasmid pTi15955", *Plant Mol. Bio.* (1983) 2:335–350.
Comai et al., "Expression in Plants of a Mutant aroA Gene from *Salmonella typhimurium* Confers Tolerance to Glyphosate", *Nature* (1985) 317:741–744.
Sibi et al., "Increase in the Rate of Recombinants in Tomato (*Lycopersicon esculentum L.*) After In vitro Regeneration", *French Theor. Appl. Genet.* (1984) 68: (4) 317–321.
Seeni and Gnanam, "In vitro Regeneration of Chlorophyll Chimeras in Tomato (*Lycopersicon esculentum*)" *Canadian J. Botany* (1981) 59:(10) 1941–1943.
Vnuchkova, *Fiziol Rast* (Moscow, USSR) (1977) 24:(5) 1094–1100.
Garfinkel and Nester, "*Agrobacterium tumefaciens* Mutants Affected in Crown Gall Tumorigenesis and Octopine Catabolism", *J. Bacteriol.*(1980) 144:732–743.
Ooms et al., "Octopine Ti–Plasmid Deletion Mutants of *Agrobacterium tumefaciens* with Emphasis on the Right Side of the T–Region", *Plasmid* (1982) 7:15–29.
Ooms et al., "Crown Gall Plant Tumors of Abnormal Morphology, Induced by *Agrobacterium tumefaciens* Carrying Mutated Octopine Ti Plasmids: Analysis of T–DNA Functions", *Gene* (1981) 14:33–50.
Hoekema et al., "A Binary Plant Vector Strategy Based on Separation of vir– and T–region of the *Agrobacterium tumefaciens* Ti–plasmid", *Nature* (1983) 303:179–181.
Cashmore et al., "Import of Polypeptides into Chloroplasts", *Biotechnology* (1985) 3:803–808.
Wickner and Lodish, "Multiple Mechanisms of Protein Insertion Into and Across Membranes", *Science* (1985) 230:400–407.
Hanahan, "Studies on Transformation of *Escherichia coli* with Plasmids", *J. Mol. Biol.* (1983) 1616:557–580.

Primary Examiner—David T. Fox
Attorney, Agent, or Firm—Rae-Venter Law Group P.C.

[57] ABSTRACT

Plant species are produced by cocultivation transformation of cotyledon shoot cultures with a foreign gene followed by regeneration of plants from transformed cells, thereby producing plants capable of expressing the foreign gene. Particularly, tomato shoot cultures are employed and are transformed employing a manipulated Agrobacterium transformation system, followed by regeneration of the transformed plant tissue into plants.

22 Claims, No Drawings

OTHER PUBLICATIONS

Nester and Kosuge, "Plasmids Specifying Plant Hyperplasias", *Ann. Rev. Microbiol.* (1981) 35:531–565.

Jorgensen et al., "A Restriction Enzyme Cleavage Map of Tn5 and Location of a Region Encoding Neomycin Resistance", *Mol. Gen. Genet.* (1979) 177:65–72.

Vieira and Messing, "The pUC Plasmids, an M13mp7-derived System for Insertion Mutagensis and Sequencing with Synthetic Universal Primers", *Gene* (1982) 19:259–268.

Knauf and Nester, "Wide Host Range Cloning Vectors: A Cosmid Clone Bank of an Agrobacterium Ti Plasmid", *Plasmid* (1982) 8:45–54.

Yanisch-Perron et al., "Improved M13 Phage Cloning Vectors and Host Strains: Nucleotide Sequences of the M13mp18 and pUC19 Vectors", *Gene* (1985) 33:103–119.

White and Nester, "Hairy Root: Plasmid Encodes Virulence Traits in *Agrobacterium rhizogenes*", *J. Bacteriol.* (1980) 141:1134–1141.

Taylor et al, "Transcription of *Agrobacterium rhizogenes* A4 T–DNA", *Mol. Gen. Genet.* (1985) 201:546–553.

Huffman et al., "Hairy–Root–Inducing Plasmid:Physical Map and Homology to Tumor–Inducing Plasmids", *J. Bacteriol.* (1984) 157:269–276.

de Framond et al., "Mini–Ti: A New Vector Strategy for Plant Genetic Engineering", *Biotechnology* (May 1983) 262–267.

Dellaporta et al., "A Plant DNA Minipreparation Version II", *Plant Mol. Biol. Rep.* (1983) 1:19–21.

Melton et al., "Efficient In vitro Synthesis of Biologically Active RNA and RNA Hybridization Probes from Plasmids Containing a Bacteriophage SP6 Promoter", *Nucleic Acids Research* (1984) 12:7035–7056.

Fillatti et al., "Efficient Transfer of a Glyphosate Tolerance Gene into Tomato Using a Binary *Agrobacterium tumefaciens* Vector", *Biotechnology* (1987) 5:726–730.

Bevan, M. 1984. Nucleic Acids Research 12(22): 8711–8721.

TRANSFORMATION AND FOREIGN GENE EXPRESSION WITH PLANT SPECIES

CROSS REFERENCE TO RELATED APPLICATIONS

This application is a continuation-in-part of application Ser. No. 07/404,723 filed on Sep. 8, 1989, now abandoned, which is a continuation-in-part of application Ser. No. 06/872,532 filed Jun. 10, 1986, now abandoned, which disclosure is hereby incorporated by reference.

BACKGROUND OF THE INVENTION

1. Field of the Invention

A method is provided for improving the genotypes and the phenotypes of plants. This method incorporates an Agrobacterium transformation system on plant cotyledon tissue, particularly cotyledons previously treated with medium from plant feeder cells. This method may be used for efficiently transforming plants to provide enhanced capabilities and/or novel phenotypes.

2. Background of the Invention

Breeding methods for plants have been limited due to the difficulty of moving genes between plant species. Therefore, the development of a method for genetic engineering with plant species is an attractive possibility. However, plant cells are substantially different from other types of cells in their requirements for a transforming system. First, unlike unicellular microorganisms, the plant cells have a low rate of proliferation. Second, the plant cells are much more sensitive to their environment in relation to viability, proliferation and regeneration to plant. Third, in order to determine whether the foreign gene has been functionally integrated into the plant cell, it is necessary to establish that the regenerated plant expresses the gene product. Finally, the plant cell has a strong rigid cell wall, making genetic engineering more difficult.

Long time intervals are involved between the manipulation of the plant cells and the demonstration of effective expression of the gene. It is therefore of interest to develop a system for transformation of plant cells and efficient regeneration of transgenic plants from the transformed cells.

BRIEF DESCRIPTION OF THE RELEVANT LITERATURE

A. L. Gunay et al., *Plant Science Letters* (1978) 11:365–372, described in vitro regeneration from red pepper cotyledons. J. R. Liu et al., *Plant Cell Organ Culture* (1983) 2:293–304, described regeneration from apple seedling explants including cotyledons. B. R. Thomas et al., *Theor. Appl. Genet.* (1981) 59:215–219, describes the regeneration media for tomato. The 1985 Calgene U.S. patent application Ser. No. 798,050 by Fillatti et al. describes the Agrobacterium of the present invention. The use of *A. tumefaciens* for transforming plants employing leaf disks is described in Horsch et al., *Science* (1985) 228:1229–1231. See also, Herrera-Estrella et al., *Nature* (1983) 303:209–213; Fraley et al., *Proc. Natl. Acad. Sci. U.S.A.* (1983) 80:4803–4807; and Bevan et al., *Nature* (1983) 304:184–187. The glyphosate resistant aroA gene is described in Stalker et al., *J. Biol. Chem.* (1985) 260:4724–4728, while transcriptional initiation and termination regions are described by deGreve, *J. Mol. Appl. Genet.* (1983) 1:499–511; Salomon et al., *EMBO J.* (1984) 3:141–146; Velten et al., ibid. (1984) 3:2723–2730; Garfinkel et al., *Cell* (1983) 27:143–153; and Barker et al., *Plant Mol. Bio.* (1983) 2:335–350. Comai et al., *Nature* (1985) 317:741–744, describe the expression of a mutant aroA gene from *Salmonella typhimurium* in plants providing tolerance to glyphosate. Other reports discussing tomato cotyledon regeneration include: Orsay, *French Theor. Appl. Genet.* 68 (4), 1984, 317–322; Seeni, S. et al., *Canadian J. Botany* 59 (10), 1981, 1941–1943; and Vnuchkova, V. A., Fiziol Rast (Moscow, USSR), 24 (5), 1977, 1094–1100.

SUMMARY OF THE INVENTION

Methods and compositions are provided for efficiently obtaining transgenic plants. It is a feature of this invention to use as a source of cells for transformation cotyledon sections, preferably sections from cotyledons obtained from seeds grown under sterile conditions. The method involves transforming the plant cells by cocultivating cotyledon sections using disarmed Agrobacteria comprising a DNA sequence of interest. Generally, the plant cotyledon tissue which is preincubated with medium conditioned by plant feeder cells prior to transformation. The method results in a high proportion of normal transformed cells, which are then efficiently regenerated into plants yielding both plants and seeds. The technique provides for stable expression of introduced genes, particularly foreign genes providing plants having altered phenotypes.

DESCRIPTION OF THE SPECIFIC EMBODIMENTS

Novel procedures and products are provided involving the introduction of novel nucleotide constructs into cells of plant species using plant cotyledon tissue. Regeneration of the transformed cells into plants, provides plants which express one or more genes present in the construct, so as to provide at least one property for the plant different from the original cultivar, particularly a phenotypic property.

The method employed uses injured cotyledon tissue, preferably preincubated with conditioned medium. The use of cotyledon tissue as a source of cells for transformation offers several advantages over other tissue sources, such as leaf and stem. The advantages include uniformity of tissue and a source of sterile tissue. Explant material obtained from growth chamber or greenhouse grown plants (i.e. material which is not derived from in vitro grown explant material) must be surface sterilized prior to use. Surface sterilization of the tissue can damage the cells and thus interfere with the regeneration potential of the tissue.

The preincubated plant cotyledonous tissue is cocultivated in an appropriate nutrient medium with disarmed transformed Agrobacterium having plant cell transformation capability and a DNA construct joined to a T-DNA border. The construct can be prepared by joining DNA fragments from diverse sources. It includes a gene capable of at least transcription in the host cell. The cocultivated cells are transferred to regeneration medium, normally having a bacteriocide selective for transformed cells, when a selectible marker is included in the construct. After shoots form, the shoots are transferred to a selective rooting medium to provide a complete plantlet. The plantlet may then be grown to provide seed, cuttings, or the like for propagating the novel plants. The method provides for high efficiency of transformation of plant cells and regeneration of plants from the cells.

The plant species which can be transformed are those plants employed for commerical purposes and subject to cultivation and management. Such plants include vegetables, fruits, ornamental flowers, woody species etc., such as the following di-, and polycotyledonous species: tomato, pinus, pepper, lettuce, cucumber, soybean, brassica (rapeseed), poplar, ornamental flowers, and the like.

Sterile seeds are employed as a source for plant cotyledons. The cotyledons may be mature or immature. The cotyledons may have protruded from the seed or be present in the seed and obtained by cutting the seed and dissecting the cotyledons from the seed coat. For many plants, the cotyledons will have protruded, but for a few, e.g., pine, the cotyledons may be immature and obtained from within the seed.

Germination for protruding cotyledons will usually be at least four days in an appropriate germination medium and fewer than about fifteen days, preferably from about six to eight days. The resulting cotyledon tissue is used as a source of tissue for transformation, being injured to provide sites of regeneration. Regeneration occurs better at injured cell sites proximal to the basal site. Conveniently, the cotyledon may be cut into sections, usually three, and the middle section employed for transformation.

The injured cotyledon tissue is transferred to a feeder plate. The cells of the feeder plate act as a nurse culture for the injured cotyledon tissue and enhance the efficiency of transformation. Any convenient plant cell suspension may be employed as the feeder culture, such as Nicotiana (tobacco) or corn, particularly the former. While tobacco feeder cells are preferred for certain crops, e.g., tomato, corn or other plant feeder cells are also useful as feeder cells. The preincubation with the feeder cell conditioned medium is usually at least six hours and not more than about 48 hours, 12 to 24 hours usually being employed. Preferably the preincubation is carried out in low light, generally 40–50 micro Einsteins, but no greater than 80 micro Einsteins.

The feeder plates are prepared by employing a plant suspension culture, e.g., Nicotiana cells, about $10^4$–$10^{10}$ cells/ml, usually about $10^6$ cells/ml, in a soft agar medium, generally having from about 0.5 to 1% agar and containing an appropriate growth medium, such as Murashige and Skoog minimal organic medium and appropriate amounts of hormones, i.e., auxins, such as 2,4-dichlorophenoxyacetic acid (2,4-D), kinetin and vitamins, such as thiamine, with a medium appropriately buffered in the range from 5 to 6, preferably about 5.5. The kinetin and thiamine will generally be about 0.075 to 1.5 mg/L, while the 2,4-D will generally be about 0.05 to 0.2 mg/L. Desirably, the feeder plates are prepared prior to being used, usually at least about one, more usually two days, prior to being used.

After the feeder suspension cells have grown for at least 24 hours, generally 24 to 48 hours, the feeder plates (soft agar layers) are covered with a porous cover to prevent the feeder cells from coming into contact with the cotyledon explants. This porous cover allows the explants to be bathed in conditioned medium. This can be readily achieved employing a sterile filter paper disk such as, for example, #1 Whatman filter paper and the like. The cotyledons are then allowed to preincubate, followed by transfer to a broth culture of the Agrobacteria strain containing the DNA construct for transformation of the plant cells, said Agrobacteria having the genetic capability for transfer of the construct into the plant cells. Generally, the number of bacteria are from about $10^6$ to $10^{10}$/ml, usually about $10^8$ to $10^{10}$/ml and will vary with the particular strain.

The contact with the Agrobacteria in the bacterial broth culture, e.g., MG/L (same as LBMG; see Garfinkel et al., *J. Bacteriol.* (1980) 144:732–743), is usually at least about 1 minute and not more than about 1 hour, usually averaging about 30 minutes. The cotyledon sections are then transferred from the bacterial broth, excess surface liquid removed and the cotyledon sections returned to the feeder plates. Bacterial cocultivation on the feeder plates will usually be at least 6, usually at least 12 hours and not more than about four days, averaging about one to three days. After cocultivation with the bacteria, the cotyledon segments are transferred to regeneration medium.

The regeneration medium will usually contain a bacteriocide, e.g., carbenicillin (500 mg/l), and may contain a selective reagent for selecting transformed cells. For example, with the kanamycin resistance gene (APH3'II), kanamycin will be added to at least about 30 mg/l and usually not more than about 500 mg/l, preferably from about 50 to 100 mg/l, in the selective medium. The regeneration medium includes an appropriate salt source, such as Murashige-Skoog salts medium, a carbon source, e.g., sucrose, with appropriate other additives, such as hormones, e.g., zeatin, etc., at about 0.75–2.25 mg/l, myo-inositol at about 50–200 mg/l, etc. Also, a vitamin supplement may be added, e.g. Nitsch vitamins, at about 0.5 to 1.5 ml/l of 1000× stock, (usually 1.0 ml/l) as is conventional in regeneration media. The 1000× stock of Nitsch vitamins contains in a 100 ml final volume: 50 mg thiamine HCl, 200 mg glycine, 50 mg nicotinic acid, 50 mg pyridoxine HCl, 50 mg folic acid, 5 ml biotin and water to volume. The carbon source will be present in from 10 to 30 g/l. Conveniently, the regeneration medium contains about 0.5 to 1.0% agar, with the regeneration medium being buffered at about pH 6±0.5.

In 2 to 3 weeks shoots normally develop. When the shoots are approximately 1 to 2 cm, they are excised at the base and transferred to a rooting medium, for example, MSSV medium and the like, which may be the same medium as that on which the seedlings were grown, with carbenicillin (usually 50 mg/l) and kanamycin sulfate (usually 50 mg/l) added. Roots generally develop within 7–14 days. The resulting plantlets can then be transfered to soil and grown into plants.

Various disarmed strains may be employed which provide for efficient transformation of plants. The disarmed strains will lack in whole or in part the T-DNA region, particularly the hormone gene region, and may also lack one or both borders and the region associated with the expression of opines. Desirably, the Ti- or Ri-plasmid lacks a region of significant homology with the construct sequence.

The Agrobacterium system which is employed involves the use of a disarmed strain, for example, *A. tumefaciens* PC2760 (G. Coms et al., *Plasmid* (1982) 7:15–29; G. Coms et al., *Gene* (1981) 14:33; A. Hoekema et al., *Nature* (1983) 303:179–181; European Patent Application 84-200239.6, 2424183).

The Agrobacteria to be employed in the transforming of the plant cell will be transformed with a wide host range plasmid that can shuttle DNA from *E. coli* into the Agrobacteria. This can be achieved by having a P-1 incompatibility plasmid replicon, e.g., RK2, and a plasmid replicon capable of providing multicopies in *E. coli*, usually at least 5, preferably at least 10, and up to 200 copies in *E. coli*. The wide host range plasmid will be characterized by having at least one T-DNA border sequence, particularly the right border sequence, or conveniently having both border sequences separated in one direction by the various constructs intended to be integrated into the plant species genome.

The transformed plant cells may be cells in culture, may be present as a disorganized mass in callus, organized as leaf explants, shoot cultures, seeds, fruits, leaves, roots, or organized as a whole plant. The foreign construct will normally be present in all or substantially all of the cells of the plant tissue, but expression may be limited to particular cells or particular stages in the development of the plant. The foreign construct will include transcriptional and translational initiation and termination signals, with the initiation signals 5' to the gene of interest and the termination signals 3' to the gene of interest.

The transcriptional initiation region which includes the RNA polymerase binding site (promoter) may be native to the plant host or may be derived from an alternative source, where the region is functional in the tomato host. Other sources include the Agrobacterium T-DNA genes, such as the transcriptional initiation regions for the biosynthesis of nopaline, octopine, mannopine, or other opine transcriptional initiation regions, transcriptional initiation regions from plants or other plant species than the host species, transcriptional initiation regions from viruses, particularly host specific viruses, or partially or wholly synthetic transcription initiation regions.

The transcriptional initiation regions may not only include the RNA polymerase binding site, but also regions providing for regulation of the transcription, where the regulation involves chemical or physical repression or induction, e.g., metabolites or light, or regulation based on cell differentiation, such as associated with leaves, roots, seed, or the like. Thus, the transcriptional initiation region or the regulatory portion of such region is obtained from an appropriate gene, which is regulated, for example, the 1,5-ribulosebiphosphatecarboxylase gene, which is light-induced, stress-induced genes, heat shock genes, which are temperature regulated, wound induced genes, meristem specific genes, etc.

The 3' termination region may be derived from the same gene as the,transcriptional initiation region or a different gene. For example, where the gene of interest has a transcriptional termination region functional in the tomato species, that region may be retained with the gene.

An expression cassette is constructed which includes the transcriptional initiation region, the gene of interest under the transcriptional regulational control of the transcriptional initiation region, the initiation codon, the coding sequence of the gene, with or without introns, the translational stop codons, followed by the transcriptional termination region, which will include the terminator, and normally includes a polyadenylation signal sequence, and other sequences associated with transcriptional termination. The direction is 5'–3' in the direction of transcription. The cassette will usually be less than about 10 kb, frequently less than about 6 kb, usually being at least about 1 kb, more usually being at least about 2 kb.

The gene of interest may be derived from a chromosomal gene, cDNA, a synthetic gene, or combinations thereof. Where the expression product of the gene is to be located in other than the cytoplasm, the gene will usually be constructed to include particular amino acid sequences which result in translocation of the product to a particular site, which may be an organelle, such as the chloroplast, mitochondrion or nucleus, the cell plasma membrane, or may be secreted into the periplasmic space or into the external environment of the cell. Various secretory leaders, membrane integrator sequences, and translocation sequences for directing the peptide expression product to a particular site are described in the literature. See, for example, Cashmore et al., *Biotechnology* (1985) 3:803–808, Wickner and Lodish, *Science* (1985) 230:400–407.

Genes of inlerest for use in plant species include a wide variety of phenotypic and non-phenotypic properties. Among the phenotypic properties are enzymes which provide for resistance to stress, such as dehydration resulting from heat and salinity, resistance to insects, herbicides, toxic metal or trace elements, or the like. Resistance may be as a result of a change in the target site, enhancement of the amount of the target protein in the host cell, the increase in one or more enzymes involved with the biosynthetic pathway to a product which protects the host against the stress, and the like. Genes may be obtained from prokaryotes or eukaryotes, bacteria, fungi, e.g., yeast, viruses, plants, mammals or be synthesized in whole or in part. Illustrative genes include glyphosate resistant 3-enolpyruvylphosphoshikimate synthase gene, nitrilase, genes in the proline and glutamine biosynthetic pathway, metallothioneins, thioesterase II, acyl carrier protein, acetyl transacylase, etc. Other genes of interest may be involved with regulation of growth, such as manipulations of source/sink (carbon partitioning) relations, e.g., changes in solids content, or hormonal regulation, photosynthetic efficiency, such as altering the efficiency of RuBP carboxylase, or changing the quality of the plant taste or nutritional value, altering solid liquid ratios, viscosity or the number, size, color and abrasion resistance or firmness of the plant fruit.

One or more cassettes may be involved, where the cassettes may be employed in tandem for the expression of independent genes which may express products independently of each other or may be regulated concurrently, where the products may act independently or in conjunction.

The expression cassette to be transformed into plant cells by means of Agrobacterium, will be bordered usually within at least about lkb by the right or both T-DNA borders. These borders may be obtained from any Ti- or Ri-plasmid and may be joined to the expression cassette by conventional ways. The expression cassette may be constructed so as to be directly transferred from a plasmid other than a Ti- or Ri-plasmid or may become integrated into the T-DNA region of a Ti- or Ri-plasmid through homologous recombination. Thus, the expression cassette could have DNA sequences at one or both borders of the expression cassette homologous with sequences present in the T-DNA region of the Ti- or Ri-plasmid. The Ti-plasmid will be disarmed so as to lack the genes expressing the protein product(s) essential to gall formation.

The expression cassette will normally be carried on a vector having at least one replication system. For convenience, it is common to have a replication system functional in *E. coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. These plasmids are particularly effective with disarmed Ti-plasmids for transfer of T-DNA to the plant species host.

In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant species host. The markers may be protection against a biocide, such as antibiotics, toxins, heavy metals, or the like; or complementation, imparting prototrophy to an auxotrophic host. Various genes which may be employed include neomycin phosphotransferase (NPTII), hygromycin phosphotransferase (HPT), chloramphenicol aminotransferase (CAT), nitrilase, gentamicin resistance gene, etc. For plant host selection, markers of particular interest include NPTII, providing kanamycin resistance or G418 resistance, HPT, providing hygromycin resistance, CAT, providing chloramphenicol resistance, mutated aroA gene providing glyphosate resistance, etc.

The various fragments comprising the various constructs, expression cassettes, markers, and the like may be introduced consecutively by restriction enzyme cleavage of an appropriate replication system, and insertion of the particular construct or fragment into the available site. After ligation and cloning the vector may be isolated for further manipulation. All of these techniques are amply exemplified in the literature and find particular exemplification in Maniatis et al., *Molecular Cloning: A Laboratory Manual*, Cold Spring garbor Laboratory, Cold Spring Harbor, N.Y., 1982.

The transformed plant cells containing the desired construct may now be isolated by appropriate selective means. The cells may be grown onto callus in a selective medium, which medium may contain a biocide, e.g., an antibiotic such as G418, hygromycin, bleomycin, etc., depending upon the particular marker included in the construct to provide for resistance. The concentration of the biocide will vary in accordance with plant cell susceptability. Where no marker is used or the expression of the marker gene proves inadequate for selection, transformed cells may be detected by Southern, Northern, or Western blots for detecting nucleic acid sequences and proteins.

Once the callus forms shoots, the shoots may be transferred to a rooting medium to produce plantlets which express the gene of interest.

The resulting plant may have a wide variety of desirable phenotypes, such as resistance to adverse conditions, e.g., heat, salinity, herbicides, etc, improved processing characteristics, improved organoleptic properties, overproduction of particular plant products, e.g. plant oils, production of bacterial or mammalian proteins and the like.

The following examples are offered by way of illustration and not by way of limitation.

EXPERIMENTAL

*E. coli* strain MM294 (Hanahan, *J. Mol. Biol.* (1983) 116:557–580) was used as the host for binary vectors containing the pRK290 type replicon. Agrobacterium strain C58 has been described supra. PC2760 is another designation for Agrobacterium strain LBA4404 (Hoekema et al., *Nature* (1983) 303:179–180). Strain K12 was generated by transforming pTiA6 into strain All4 (NT1) (Nester and Kosuge, *Ann. Rev. Microbiol.*, (1981) 35:531, Hoekema et al., *Nature* (1983) 303:179). Levels of antibiotics used with *E. coli* in mg/l were 30 for kanamycin, 50 for chloramphenicol, 300 for penicillin, 10 for tetracycline and 20 for gentamicin. Unless otherwise indicated, levels of antibiotics used with Agrobacteria in mg/l were 100 for kanamycin or gentamicin and 50 for carbenicillin or chloramphenicol.

Laboratory Procedures

Restriction enzymes and T4 ligase were obtained from commercial sources and used according to manufacturers' recommendations. Standard methods of cloning and molecular analysis were performed as described in Maniatis et al., supra.

Deposit

*E. coli* containing plasmid C2110 pCGN587/85 were deposited with the American Type Culture Collection (ATCC) 12301 Parklawn Drive, Rockville, Md., 20852 on May 20, 1986. The cultures were given Accession Number ATCC 67118.

EXAMPLE I

For all the cocultivation studies, a binary disarmed strain of *A. tumefaciens* designated LBA4404/587/85 was used. To prepare the strain, a binary vector plasmid, PPMG85/587 was introduced into strain LBA4404 as described below. This vector plasmid carries a modified T-DNA with three chimeric genes. Two of the genes code for neomycin phosphotransferase (APH3'II) enzyme activity which confers resistance to the antibiotic kanamycin. One of the APH3'II genes is spliced to the octopine synthase promoter and the other to the mannopine synthase promoter. The two APH3'II genes were engineered into the T-DNA to allow for direct selection of transformed tissue. The third chimetic gene fusion contains a mutant aroA gene isolated from *Salmonella typhimurium* which confers tolerance to the herbicide glyphosate. This gene has been spliced to the mannopine synthase promoter to obtain expression in plants.

Plasmid Constructions

The BglII-SmaI fragment of Tn5 containing the entire structural gene for APH3'II (Jorgensen et al., *Mol. Gen.* (1979) 177:65) was cloned into pUC8 (Vieira and Messing, *Gene* (1982) 19:259), converting the fragment into a HindIII-EcoRI fragment, since there is an EcoRI site immediately adjacent to the SmaI site. The PstI-EcoRI fragment containing the 3' portion of the APH3'II gene was then combined with an EcoRI-BamHI-SalI-PstI linker into the EcoRI site of pUC7 (pCGN546W). Since this construct does not confer kanamycin resistance, kanamycin resistance was obtained by inserting the BglII-PstI fragment of the APH3'II gene into the BamHI-PstI site (pCGN546X). This procedure reassembles the APH3'II gene, so that EcoRI sites flank the gene. An ATG codon was upstream from and out of reading frame with the ATG initiation codon of APH3'II. The undesired ATG was avoided by inserting a Sau3A-PstI fragment from the 5'-end of APH3'II, which fragment lacks the superfluous ATG, into the BamHI-PstI site of pCGN546W to provide plasmid pCGN550.

The EcoRI fragment containing the APH3'II gene (1ATG) was then cloned into the unique EcoRI site of pCGN451, which contains an octopine synthase cassette for expression to provide pCGN552(1ATG). The octopine synthase cassette contains about 1556 bp of the 5' non-coding region fused via an EcoRI linker to the 3' non-coding region of the octopine synthase gene of pTiA6. The pTi coordinates are 11,207 to 12,823 for the 3' region and 13,643 to 15,208 for the 5' region as defined by Barker et al., *Plant Mol. Biol.* (1983) 2:325.

The 5' fragment was obtained as follows: A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were size fractionated; the fractions were then cloned and sequenced.

In one case, the entire coding region and 10 bp of the 5' non-translated sequences were removed leaving the 5' non-transcribed region, the mRNA cap site and 16 bp of the 5' non-translated region (to a BamHI site) intact. This small fragment was obtained by size fractionation on a 7% acrylamide gel. Fragments approximately 130 bp long were eluted from the gel. This size-fractionated DNA was ligated into M13mp9. Several clones were sequenced and the sequences compared to the known sequence of the octopine synthase gene. The M13 construct was designated pI4, which plasmid was digested with BamHI and EcoRI to provide the small fragment which was ligated to a XhoI to BamHI fragment containing upstream 5' sequences from pTiA6 (Garfinkel and Nester, *J. Bacteriol.* (1980) 144:732) and to an EcoRI to XhoI fragment containing the 3' sequences. The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of the HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550 bp of 5' non-transcribed sequence including the right border of the T-DNA, the mRNA cap site and 16 bp of 5' non-translated sequence) and the 3' region (which contains 267 bp of the coding region, the stop codon, 196 bp of 3' non-translated DNA, the polyA site and 1,153 bp of 3' non-transcribed sequence).

Plasmid pCGN451, which had the ocs 5' and the ocs 3' in the proper orientation, was digested with EcoRI and the EcoRI fragment from pCGN551 containing the intact kanamycin resistance gene was inserted into the EcoRI site to provide pCGN552 which had the kanamycin resistance gene in the proper orientation. This ocs/KAN gene was used to provide a selectable marker for the trans type binary vector pCGN587.

The 5' portion of the engineered octopine synthase promoter cassette consists of TiA6 DNA from the XhoI fragment at bp 15208-13644 (Barker's numbering), which also contains the T-DNA boundary sequence (border) implicated in T-DNA transfer. In the plasmid pCGN587, the ocs/KAN gene from pCGN552 provides a selectable marker as well as the right border. The left boundary region was recloned from the HindIII-EcoI fragment as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BglII fragment of pVCK102 (Knauf and Nester, *Plasmid* (1982) 8:45), creating pCGN585. By replacing the smaller SalI fragment of pCGN585 with the XhoI fragment from pCGN552 containing the ocs/KAN gene, pCGN587 was obtained.

Construction of pPMG85

To construct pPMG85, the mannopine synthase gene (mas) 5' region from pTiA6 (Salomon et al., *EMBO J.* (1984) 3:141–146). The gene was obtained from a cosmid clone carrying the T-DNA of pTiA6 called pVCK232 (Knauf and Nester, *Plasmid* (1982) 8:45–54). pVCK232 was digested with EcoRI and one of the resulting fragments called Eco13 or EcoC was cloned in pACYC184 to provide plasmid pCGN14. Digestion of pCGN14 with ClaI and SphI yielded a mixture of fragments with the desired fragment resulting from cleavage at the ClaI site (20128) to the SphI site (21562) (Barker et al., *Plant Mol. Bio.* (1983) 2:335–350). This fragment contains the mas 5' region and was cloned in pUC19 (Yanisch-Perron et al., *Gene* (1985) 33:103–119) which had been linearized with SphI and AccI to provide plasmid pCGN40. The aroA BamHI fragment from pPMG34 (Stalker et al., *J. Biol. Chem.* (1985) 260:4724–4728) was cloned in the proper orientation in pCGN40, where the aroA gene was fused to the mas promoter region, providing pPMG67.

To provide a polyadenylation signal, the tml 3' region of pTiA6 (Garfinkel et al., *Cell* (1983) 27:143–153) was used. A T-DNA BamHI fragment (9062–13774; Barker numbering) containing such region was cloned from pVCK232 in pACYC184 in the orientation where nucleotide 13774 was proximal to the HindIII site of the vector. The resulting plasmid was digested with SmaI, which cleaves at nucleotide 11210 (Barker numbering) of the tml 3' region and an octomeric XhoI linker (New England Biolabs) inserted. The resulting plasmid pBamX was digested with HindIII and XhoI. A fragment containing most of the mas 5' region and the aroA gene, obtained by digestion of pPMG67 with HindIII and SalI, was cloned into the linearized pBamX. The resulting plasmid, pPMG73, contained a 5'-mas-aroA-tml-3' hybrid gene.

To allow for efficient selection in Agrobacterium, the kanamycin resistance gene from pUC4K (Vieira and Messing, *Gene* (1982) 19:259–268) was excised from SalI and cloned in a XhoI site present in the aroA distal end of the mas 5' region giving pPMG76. A 2.0 kb EcoRI fragment in the Hind17 region of pRiA4T-LT-DNA (White and Nester, *J. Bacteriol.* (1980) 141:1134; Taylor et al., *Mol. Gen. Genet.* (1985) 201:546) was cloned in the chloramphenicol resistance gene EcoRI site of pPMG76 yielding pPMG82.

To allow selection of transformed plants on kanamycin, a mas-npt hybrid gene was constructed. (See Velten et al., *EMBO J.* (1984) 3:2723–2730 for an analogous construction.) The mas 5' region was excised from pCGN40 by digestion with EcoRV (21552; Barker numbering) and EcoRI (in the pUC19 polylinker) and cloned in pCGN451 digested with SmaI and EcoRI. The restriction deletes all of the ocs 5' region from pCGN451 and inserts the mas 5' region in its place. In addition, part of the pUC19 polylinker from XbaI to EcoRI was placed between the mas promoter region and the ocs polyadenylation site, allowing a choice of different sites for insertion of genes to be expressed. In the EcoRI site of this plasmid pCGN46, an EcoRI fragment of pCGN552, carrying the Tn5 npt gene (Rothstein et al., *Cell* (1980) 19:795–805), was inserted where an untranslated ATG sequence in the 5' region had been removed. The hybrid mas-npt-ocs gene was excised by digestion with XhoI and cloned in the SalI site of pPMG82 resulting in pPMG85.

Plasmid pPMG85 contained, beginning from the EcoRI site, an EcoRI-HindIII 1.5 kb fragment from pACYC184 and, going clockwise, the bacterial kanamycin resistance gene from pUC4K, the mas 5' region nucleotides 21476 to 20128, oriented in the clockwise direction, a BamHI-SalI aroA-containing fragment from pPMG34, the tml 3' region from nucleotides 11207 to 9062, a BamHI-SalI fragment from the tetracycline resistance gene of pACYC184, the npt gene from pCGN552, a 2.5 kb SalI-EcoRI fragment from pACYC184 and a 2 kb EcoRI fragment from pRIA4 on the BglII-HindIII-17 fragment (Huffman et al., *J. Bacteriol.* (1984) 157:269–276).

EXAMPLE II

Tomato Transformation and Regeneration

Cotyledon Preparation

*Lycopersicon esculentum* cv UC82 (Department of Vegetable Crops, University of California, Davis, Calif. 95616) seed were surface sterilized for 5 min in a 0.05% sodium hypochlorate solution and plated onto tomato seedling medium (medium containing Murashige and Skoog salts, 3% sucrose and 0.8% Bacto agar). All cultures were grown in a controlled environment room at 25° C.±2° C., using cool white fluorescent light 50 micro Einsteins per meter$^2$ per second (50 $\mu Em^{-2}S$) for 16-hr light day cycles.

Feeder Plates

Tobacco feeder plates were prepared 2 days prior to use by piperting 0.5 ml of tobacco suspension cultures (~10$^6$ cell/ml) onto Petri dishes (100×25 mm) containing 50 ml of tobacco suspension medium (Murashige minimal organics medium (K.C. Biologicals) supplemented with 2,4-D (0.1 mg/l), kinetin (0.1 mg/l), thiamine hydrochloride (0.9 mg/l), potassium acid phosphate (200 mg/l), and Difco Bacto agar (0.8% pH 5.5). After 2 days, a sterile filter paper disk (Whatman 3 mm) was placed on top of the tobacco cells. The filter paper disks had been prewashed in distilled water and autoclaved in liquid tobacco suspension medium (suspension medium prepared without agar).Tripartite mating,

*Agrobacterium tumefaciens* strain 2760/587/85 was prepared as follows. The plasmids pCGN587 and pPMG85 were transformed into *E. coli* C2110 (polA1) and cointegrates selected by kanamycin and glyphosate resistance, de Framond et al., *BioTechnology*, May 1983, pp. 262–267. Bacterial matings were performed using two *E. coli* strains and one Agrobacterium strain. One *E. coli* strain (MM294) harbored pRK2073 which provided mobilization functions and the other strain (C2110) carried the plasmid with a kanamycin resistance marker to be transferred into the Agrobacteria. The two *E. coli* strains were grown overnight at 37° C. with shaking in LB broth. The Agrobacterium strain was grown overnight at 28° C. in MG/L broth. Fifty microliters of each of the three strains were mixed on a nitrocellulose filter placed on an MG/L plate. The plate was incubated at 28° C. for 3 days. The mixture was then streaked onto an AB minimal medium supplemented with 100 µg/ml kanamycin and 100 µg/ml streptomycin and incubated at 28° C. for two days. Streptomycin was included to kill the two *E. coli* strains. Single colonies were picked and purified by two more streakings on the above medium.

Transformation

After the tobacco feeder plates were prepared, cotyledons were cut into segments (approximately 2 cm$^2$) and preincubated on the feeder plates for 24 hrs at 25° C., under low light conditions (10 $\mu Em^2S^{-1}$). Following the preincubation period, the tomato cotyledon segments were placed into 1–5 ml of a broth culture of *A. tumefaciens* strain 2760/587/85, or 2760 diluted to the appropriate concentration. After 30 min, the segments were blotted to remove excess suspensions and replaced onto the feeder plates for 24–72 hrs of coincubation with the bacteria. The cotyledon segments were subsequently transferred to shoot regeneration medium (MS medium supplemented with 2 mg/l zeatin, 100 mg/l myo-inositol, 20 g/l sucrose, Nitsch vitamins and 0.8% agar, pH 6.0) containing 500 mg/l carbenicillin (a bacteriostatic substance) and 100 mg/l kanamycin sulfate (a selective antibiotic). After 3–4 weeks, shoots began to develop.

The shoots were excised at the base and transferred to rooting medium, which is the same as tomato seedling medium except that 500 mg/l carbenicillin and 50 mg/l kanamycin were added. Within 10–12 days, roots developed. The regenerated tomato plantlets were transplanted into 6-inch pots containing soil and grown in a growth chamber. Moist cheese cloth was draped over the newly transplanted seedlings for 3–4 days to minimize the stress associated with transplanting. Tomato plants were transferred from growth chambers to the greenhouse after 4–6 weeks.

EXAMPLE III

Molecular Analysis of Transgenic Plants

Shoots which developed and subsequently rooted on media containing the kanamycin were tested for APH3'II enzyme activity and for the presence of the aroA protein.

Aminoglycoside Phosphotransferase Analysis

An aminoglycoside phosphotransferase enzyme (APE 3'II) assay was conducted on putative transformed tomato plants and shoots. APH 3'II confers resistance to kanamycin and neomycin. APH 3'II activity was assayed (Reiss et al., *Gene* (1984) 30:211–218) employing electrophoretic separation of the enzyme from other interfering proteins and detection of its enzymatic activity by in situ phosphorylation of kanamycin. Both kanamycin and [$\gamma$-$^{32}$P] ATP act as substrates and were embedded in an agarose gel which was placed on top of a polyacrylamide gel containing the proteins. After the enzymatic reaction, the phosphorylated kanamycin was transferred to P-81 phosphocellulose ion exchange paper and the radiolabeled kanamycin finally visualized by autoradiography. The Reiss et al. method was modified in the final washing of the P-81 ion exchange paper by rinsing in 0.1 mg/ml of proteinase K. Approximately 90% of the tomato plants which developed shoots and subsequently rooted on kanamycin-containing medium tested positive for APH3'II enzyme activity. Samples of untransformed tomato plants did not exhibit any APH3'II activity.

Southern Blot Analysis

The presence of the APH3'II gene in the kanamycin-positive plants was confirmed by a Southern blot analysis. DNA was isolated from tomato plants using the protocol described by Dellaporta et al., *Plant Mol. Biol. Rep.* (1983) 1:19 as follows. Isolated DNA was digested with EcoRI, separated by gel electrophoresis, blotted onto nitrocellulose and then hybridized separately to an aroA probe, and an APH3'II probe. Procedures for restriction digestion, gel electrophoresis, Southern transfer and hybridization were as described by Maniatis et al., Molecular Cloning: A Laboratory Manual (1982) (CSH Laboratory, Cold Spring Harbor, N.Y.). The probe for the APH3'II gene and the aroA gene, respectively, were cloned in pSP64, and SP6-transcription vector (Milton et al., *Nucleic Acids Research* (1984) 12:7035–7056). The protocol recommended by the manufacturer for synthesis and hybridization was followed (Promega Biotec, Madison, Wis.). The APH3'II gene was present in all five plants tested. Based on reconstruction experiments, 1–3 intact copies of the APH3'II gene are estimated integrated into the plant genome.

Western Blot Analysis

A Western blot analysis was conducted on putative transformants to detect the presence of the bacterial EPSP synthase enzyme encoded by the aroA gene using the protocol described by Comai et al., *Nature* (1985) 317:741–744. Antibodies were obtained by conventional procedures, immunizing a rabbit with the mutated glyphosate-resistant aroA gene expression product. See U.S. Pat. No. 4,535,060, which relevant disclosure is incorporated herein by reference. Extracts of tomato plants showed a positive band for aroA protein in a Western blot (Fillatti et al., *Biotechnology* (1987) 5:725–730). A polypeptide which reacted with the anti-EPSP synthase serum and had the expected molecular weight was present in 80% of the 130 plants tested. This polypeptide was not found in control untransformed plants.

The amount of bacterial EPSP synthase protein observed varied between different transformation events.

Glyphosate Tolerance.

Progeny from self-pollinated transformants ($T_2$ generation) were used to evaluate the tolerance phenotype in greenhouse experiments and for genetic analysis. $T_2$ tomato plants were sprayed with the equivalent of 0.84 kg/ha glyphosate and then scored for tolerance after two weeks. In all cases, the distinction between tolerant and susceptible plant phenotypes was unambiguous. $T_2$ plants producing the mutant EPSP enzyme continued to grow after the herbicide treatment, while control untransformed plants died at this dosage. Commercial application rates range from 0.5 to 1.5 kg/ha.

The tolerance to susceptible ratio of the three events tested fit a 3:1 ratio, confirming that the aroA gene was iaaintained during meiosis and was inherited in a simple Mendelian fashion (see Table 1). Western blot analysis was performed on five plants possessing the tolerant phenotype and on three susceptible plants. In all cases the presence of the aroA protein was correlated with the glyphosate-tolerant phenotype. Two phenotype classes resulted after spraying the $T_2$ generation. Class A plants exhibited a higher tolerance to glyphosate (0.84 kg/ha) than Class B plants, which were approximately half the size of Class A plants, 14 days after spraying. Western blot analysis of these two phenotypic classes indicated that plants exhibiting a higher level of herbicide tolerance also produced more protein than the less tolerant plants, suggesting the tolerance phenotype is correlated to the amount of aroA protein produced.

TABLE 1

Genetic Inheritance of Glyphosate Tolerance in Tomato Plants Containing the Mutant aroA Gene

| Transfor-<br>mation | Observed<br>Ratio | | Expected<br>Ratio | | Chi-<br>square | Signifi-<br>cance |
|---|---|---|---|---|---|---|
| Event* | T** | S | T | S | Value | Level |
| 6-60 | 156.0 | 60.0 | 162.0 | 54.0 | 0.89 | 0.346 |
| 6-82 | 107.0 | 45.0 | 114.0 | 38.0 | 1.72 | 0.190 |
| 6-93 | 95.0 | 31.0 | 94.5 | 31.5 | 0.01 | 0.918 |

*All events were self-pollinated and the progeny sprayed. Expected Mendelian ratios are 3:1.
**T = tolerant, S = susceptible.

The ratio of tolerant to susceptible plants was compared to the expected ratio using a chi square analysis. The genetic inheritance of the aroA gene was determined by scoring the progeny of the transformed plants for tolerance to glyphosate sprayed at 0.84 kg/ha. The ratio of tolerant to susceptible plants fits the expected 3:1 ratio in the three cases tested indicating that the aroA gene is inherited as a single locus.

EXAMPLE IV

Effects of Bacterial Concentration and Cocultivation Time on Rate of Transformation As a measure of the transformation rate in this and the following examples, the number of explants which regenerated shoots on kanamycin-containing medium relative to the total number of explants cocultivated was used. This criterion was chosen because it was found that some of the parameters which increased the transformation rate as measured by callus initiation decreased the subsequenct regeneration rate of transformed cells.

Effect of bacterial concentration.

Cotyledon sections were cocultivated as described above with $1\times10^7$, $5\times10^7$, $1\times10^8$, $5\times10^8$ or $1\times10^9$ bacteria/ml. Over 85% of the cotyledon explants cocultivated with $5\times10^8$ bacteria/ml produced shoots on a selective regeneration medium. When the concentration of bacteria was increased or decreased five-fold, the rate of transformation and regeneration from transformed cells on a selective medium decreased as much as 30–40%. The concentration of bacteria determined optimal for strain LBA4404/587/85 was not, however, optimal for other Agrobacteria strains tested. It is necessary therefore to determine, as described above, the optimal bacterial concentration for each different strain of Agrobacteria used.

Effect of cocultivation time on the rate of transformation.

Cotyledon sections were preincubated for 24 hours, and then cocultivated with $5\times10^8$ bacteria/ml for 24, 48 and 72 hrs. After a 48-hr cocultivation period, 60% of the cotyledon explants produced shoots on kanamycin-containing medium, while only 20% and 24% of the cotyledons cocultivated for 24 and 72 hrs, respectively, produced shoots on kanamycin-containing medium (see Table 2). A 48-hr cocultivation period was optimal; however, as the optimal cocultivation time was also related to the initial bacterial concentration and the growth rate of the bacteria, the optimal length of the cocultivation period would also vary with different bacterial strains.

TABLE 2

Effect of Cocultivation Time on the Transformation Rate
Average % of Explants Regenerating Shoots on
"2Z" Medium Containing 100 mg/l Kanamycin

| | Cocultivation Time | | | | | |
|---|---|---|---|---|---|---|
| | 24 Hr | SE | 48 Hr | SE | 72 Hr | SE |
| Control*<br>(non-co-<br>cultivated) | 0 | | 0 | | 0 | |
| 2760/587/85** | 20 | 6.3 | 60 | 5.5 | 24 | 9.7 |

*57 explants/treatment
**130 explants/treatment

EXAMPLE V

Effect of Cocultivation Medium on Rate of Transformation

The effect of three different cocultivation media on the rate of transformation was tested: "2Z" medium, a regeneration medium for tomato described by Thomas and Pratt, Theor. Appl. Genet. (1981) 59:215–219; "KCMS" medium, a Murashige minimal organics medium supplemented with 2,4-D (0.2 mg/l), kinetin (0.1 mg/l), thiamine hydrochloride (0.9 mg/l), potassium acid phosphate (200 mg/l) and Difco bactoagar 0.8%; and "KCMS/Tob" which is the KCMS medium, described above, with 0.5 ml of tobacco suspension cells on top (similar to Horsch et al., 1985). Transformed kanamycin-resistant shoots were obtained on all three types of medium. When KCMS medium with a layer of tobacco suspension cells was used, however, at least a 20% increase in the number of explants producing shoots on kanamycin-containing medium (see Table 3) was obtained.

TABLE 3

Effect of the Cocultivation Medium on the Transformation Rate

| | Average % of Explants Regenerating Shoots on "2Z Medium Containing 100 mg/l Kanamycin Cocultivation Medium | | | | | |
|---|---|---|---|---|---|---|
| | KCMS/Tob | SE | KCMS | SE | 2Z | SE |
| Control* (non-cocultivated) | 0 | | 0 | | 0 | |
| 2760/587/85** | 73 | 5.5 | 48 | 2.7 | 16 | 4.8 |

*25 explants/treatment
**100 explants/treatment

EXAMPLE VI

Effect of Preincubation of Cotyledons on Rate of Transformation

Effect of preincubation of cotyledons.

Preincubation of cotyledon sections for 24 hours on the tobacco feeder plates dramatically increased the rate of transformation (see Table 4). Fifty-two percent of the explants which were preincubated for 24 hours on the feeder plates-produced shoots on kanamycin-containing media. If the cotyledon explants were not preincubated, only 17% of the explants plated produced shoots on kanamycin-containing medium. The enhancement of transformation may be due to the accumulation of substances that induce the vir genes or an increase in the rate of cell division resulting from a 24-hour exposure to 2-4,D.

TABLE 4

Effect of a Preincubation Period on the Transformation Rate

| | Average % of Explants Regenerating Shoots on "2Z" Medium Containing 100 mg/l Kanamycin Preincubatin Time | | | |
|---|---|---|---|---|
| | 0 Hr | SE | 24 Hr | SE |
| Control* (con-cocultivated) | 0 | | 0 | |
| 2760/587/85** | 17 | 5.7 | 52 | 9.4 |

*32 explants/treatment
**75 explants/treatment

EXAMPLE VII

Effect of Type of Feeder Culture on Rate of Transformation

Effect of type of feeder culture.

The number of cotyledons developing shoots following transformation with the binary vector 2760/587/85 relative to the control Agrobacterium strain 2760 and the effect of tobacco cells vs. corn cells as the feeder culture was determined. Almost 90% of the cotyledon segments cocultivated with Agrobacterium strain 2760/587/85 on medium conditioned with a tobacco feeder cells (see Table 5) developed shoots on kanamycin-containing regeneration medium. For those cotyledon segments cocultivated with Agrobacterium strain 2670/587/85 on KCMS medium conditioned with corn suspension cells or with no feeder cells, approximately 65% of the segments developed shoots as compared to 89% when the cotyledons were preincubated and cocultivated on KCMS medium with tobacco feeder cells.

EXAMPLE VIII

Transformation of Tomato Cotyledon Tissue (Alternate Method)

Sterile tomato cotyledon tissue was obtained from 7–8 day old seedlings grown at 24° C., with a 16 hr/8 hr day/night cycle in 100×25 mm petri dishes containing MSSV medium: Murachige-Skoog(MS) salts (#1117 Gibco Laboratories, New York), sucrose 30 g/l, Nitsch vitamins (Thomas, B. R., and Pratt, D. *Appl. Genet.* (1981) 59:215–219), 0.8% agar (pH 6.0). Any tomato species may be used, however, the inbred breeding line UC82B (Department of Vegetable Crops, University of California, Davis) is preferred. Seedlings from other tomato lines may develop at slightly different rates. The preferred seedlings may be identified as those in which the cotyledons have expanded and unfolded, but the first true leaf is not visible. The tips and bases of the cotyledons were removed and the center section placed onto a feeder plate for a 24-hour preincubation period in low light (approximately 40–50 micro Einsteins, but no greater than 80 micro Einsteins) at 24° C.

Feeder plates were prepared by pipeting 0.5 ml of an eight day old *Nicotiana tabacum cv xanthi* cell suspension culture ~$10^6$ cells/ml) onto 0.8% agar medium, containing MS salts, myo-inositol (100 mg.l), thiamine-HCl (1.3 mg.l), sucrose (30 g/l), potassium acid phosphate (200 mg/l) 2,4-D (0.2 mg.l), and kinetin (0.1 mg/l) (pH 5.5). The feeder plates were prepared one day prior to use. A #1 Whatman sterile filter paper (Whatman Ltd. Maidstone, England) was placed on top of the tobacco cells after the suspension cells had grown for at least one day.

Agrobacteria were grown on AB medium (AB salts [$K_2HPO_4$ 3 gm/l; $NaH_2PO4$ $H_2O$ 1.15 g/l; $NH_4Cl$, 1 g/l; Kl 0.15 g/l] glucose 5 g/l; $FESO_4$ 0.25 mg/l; $MgSO_4$ 0.246 mg/l; $CaCl_2$ 0.14 mg/l; 15 g/l agar, 100 ug/l gentamycin sulfate and 100 ug/l streptomycin sulfate) for 4–5 days. Single colonies were then inoculated into 5 mls of Mg/L broth and incubated overnight in a shaker at 30° C. and 180 rpm. Following the preincubation period, the cotyledon explants were dipped into a bacterial suspension ($5\times10^8$ bacteria/ml) for approximately 5 minutes, blotted on sterile paper towels and returned to the original tobacco feeder plates.

The explants were cocultivated with the bacteria for 48 hours on the tobacco feeders plates in low light at 24° C. The explants were then transferred to regeneration medium containing 500 mg/l of carbenicillin disodium salts and at least 100 mg/l of kanamycin sulfate. The regeneration medium was MS salts medium with zeatin (2 mg/l), myo-inositol (100 mg/l), sucrose (20 g/l), Nitsch vitamins and 0.8% agar (pH 6.0). The plates are sealed, for example with parafilm or Micropore paper tape, and again incubated at 24° C. The explants were then transferred to fresh regeneration medium containing 500 mg/l of carbenicillin disodium salts and at least 100 mg/l of kanamycin sulfate at 10 days and subsequently every three weeks. Shoots were harvested from 8 weeks onwards and placed on MSSV medium containing carbenicillin (50 mg/l), kanamycin (50 mg/l) and indole-3-butyric acid (1 mg/l). Roots developed in 7–14 days. The resulting plantlets were then transplanted into soil.

The tomato transformation/regeneration system of the subject invention was found to be rapid and efficient. Over 85% of the co-cultivated explants subsequently developed shoots on kanamycin selective medium and expressed the aroA protein. Between 2 and 10 shoots developed per explant. After 6 weeks, 10, 20 or even more shoots had developed per explant. Glyphosate spray experiments confirmed that the resulting tomato plants were resistant to 0.75 Lbs/Acre glyphosate. These above results demonstrate that plant species can be transformed efficiently, whereby foreign genes may be integrated into the plant genome and expressed, providing novel phenotypic properties. By virtue of the high transformation efficiency, successful transformations can be achieved within reasonable time periods and without unduly repetitive procedures. As evidenced by the above disclosure, plant species are provided which can be protected from herbicides, so that more efficient growth and production of crops can be achieved.

Although the foregoing invention has been described in some detail by way of illustration and example for purposes of clarity of understanding, it will be obvious that certain changes and modifications may be practiced within the scope of the appended claims.

TABLE 5

Shoot Regeneration from Co-cultivated and Control
Cotyledon Segments of *Lycopersicon esculentum* cv UC82

| | | Shoot Regeneration | | | | | |
|---|---|---|---|---|---|---|---|
| | | $N^6$ medium | | | KCMS Medium | | |
| Treatment | Feeder Culture | Number Cotyl's w/Shoots++ | Total Number Cotyl's | % Regenerating Shoots | Number Cotyl's w/Shoots | Total Number Cotyl's | % Regenerating Shoots |
| Control (no co-cultivation) | none | 0+ | 37 | 0 | 0 | 38 | 0 |
| | corn | 0 | 33 | 0 | 0 | 37 | 0 |
| | tobacco | NT* | NT | NT | 0 | 37 | 0 |
| PC2760 | none | 0 | 38 | 0 | 0 | 39 | 0 |
| | corn | 0 | 34 | 0 | 0 | 42 | 0 |
| | tobacco | NT* | NT | NT | 0 | 36 | 0 |
| PC2760/ 587/85 | none | 11 | 35 | 31.5 | 27 | 41 | 66.0 |
| | corn | 11 | 32 | 29.0 | 24 | 37 | 64.3 |
| | tobacco | NT | NT | NT | 33 | 37 | 89.3 |

NT = Not tested
+ Experiments were scored approximately 4 weeks after cocultivation.
++ All cotyledon explants were plated onto a selective regeneratin medium (2Z medium with carbenicillin 500 mg/l and kanamycin 100 mg/l).

What is claimed is:

1. A transformed *Lycopersicon esculentum* cotyledon cell, wherein said cell is present in an in vitro cell culture.

2. A method for transforming tomato species cells, said method comprising:

preincubating tomato cotyledon sections with medium conditioned by a plant cell feeder culture;

cocultivating said cotyledon sections with *Agrobacterium tumefaciens* cells comprising vir genes, wherein said Agrobacterium cells further comprise DNA construct comprising transcriptional initiation and termination regulatory regions functional in tomato plant cells and a gene other than the wild-type gene associated with at least one of said transcriptional initiation and termination regions, and at least a right T-DNA border, whereby said construct becomes integrated into the genome of cells in said cotyledon section to provide transformed tomato plant cells;

incubating said transformed tomato plant cells in a regeneration medium comprising a bacteriocide and a means for selection of said transformed tomato plant cells as the result of a marker on said DNA construct, whereby transformed tomato shoots develop; and transferring said transformed shoots to a rooting medium to produce transformed tomato plants.

3. The method according to claim 2, wherein said tomato cotyledon sections are obtained by germinating a sterile seed under substantially sterile conditions to produce a protruding cotyledon, cutting said cotyledon into at least two pieces free of the remainder of said seed and selecting the cotyledon piece closer to the seed.

4. A method according to claim 2, wherein said plant cell conditioned medium is conditioned with Nicotiana cells and said preincubation is for at least six hours and not more than about 48 hours.

5. A method according to claim 4, wherein said conditioned medium is prepared by growing about $10^4$ to $10^{10}$ Nicotiana cells/ml in a soft agar medium with hormones and vitamins for at least about one day prior to incubation of said cotyledon sections.

6. A method according to claim 2, wherein said cocultivation is for at least 12 hours in a plant cell conditioned medium.

7. A method according to claim 2, wherein the number of said Agrobacterium cells is about $10^8$ to $10^9$ cells/ml.

8. A method according to claim 7, wherein said bacterial culture contains about $5 \times 10^8$ cells/ml.

9. A method for modifying the genotype of tomato plant cells, said method comprising:

preincubating tomato cotyledon sections with medium conditioned by a plant cell feeder culture, contacting said cotyledon sections with a culture of a disarmed *Agrobacterium tumefaciens* strain comprising vir genes and a binary vector plasmid comprising at least the right T-DNA border and a gene of interest, wherein said gene of interest is under regulatory control of transcriptional initiation and termination regions functional in tomato plant cells, and wherein said gene of interest is integrated into the genome of cells in said tomato cotyledon sections, and isolating said tomato cells comprising said integrated gene of interest.

10. A method according to claim 9 wherein said binary vector plasmid further comprises a gene capable of conferring antibiotic resistance to said tomato cells.

11. A method according to claim 10 wherein said isolating is by transfer of said tomato cotyledon sections to a regeneration medium comprising said antibiotic.

12. A method according to claim 11 wherein said antibiotic is kanamycin.

13. A method according to claim 2 wherein said marker confers antibiotic resistance to said tomato cells.

14. A method according to claim 13 wherein said antibiotic is kanamycin.

15. A method according to claim 2 wherein a filter paper disk separates said tomato cotyledon sections from said plant cell conditioned medium.

16. A method for transforming tomato species cells, said method comprising:

cocultivating tomato cotyledon sections with *Agrobacterium tumefaciens* cells comprising vir genes, wherein said Agrobacerium cells further comprise a DNA construct comprising transcriptional initiation and termination regulatory regions functional in tomato plant cells and a gene other than the wild-type gene associated with at least one of said transcriptional initiation and termination regions, and at least a right T-DNA border, whereby said construct becomes integrated into the genome of cells in said cotyledon section to provide transformed tomato plant cells;

incubating said transformed tomato plant cells in a regeneration medium comprising a bacteriocide and a means for selection of said transformed tomato plant cells as the result of a marker on said DNA construct, whereby transformed tomato shoots develop; and transferring said transformed shoots to a rooting medium to produce transformed tomato plants.

17. A method according to claim 16 wherein said marker confers antibiotic resistance to said tomato cells.

18. A method according to claim 17 wherein said antibiotic is kanamycin.

19. A method for modifying the genotype of tomato plant cells, said method comprising:

contacting tomato cotyledon sections with a culture of a disarmed *Agrobacterium tumefaciens* strain comprising vir genes and a binary vector plasmid comprising at least the right T-DNA border and a gene of interest, wherein said gene of interest is under regulatory control of transcriptional initiation and termination regions functional in tomato plant cells, and wherein said gene of interest is integrated into the genome of cells in said tomato cotyledon sections, and isolating said tomato cells comprising said integrated gene of interest.

20. A method according to claim 19 wherein said binary vector plasmid further comprises a gene capable of conferring antibiotic resistance to said tomato cells.

21. A method according to claim 20 wherein said isolating is by transfer of said tomato cotyledon sections to a regeneration medium comprising said antibiotic.

22. A method according to claim 21 wherein said antibiotic is kanamycin.

* * * * *